United States Patent
Norwood et al.

(10) Patent No.: US 9,375,715 B2
(45) Date of Patent: Jun. 28, 2016

(54) HTHP PRESSURE RELIEF TOOL

(71) Applicants: John D. Norwood, Houston, TX (US); Richard F. Lukay, Houston, TX (US)

(72) Inventors: John D. Norwood, Houston, TX (US); Richard F. Lukay, Houston, TX (US)

(73) Assignee: OFI Testing Equipment, Inc., Houston, TX (US)

( * ) Notice: Subject to any disclaimer, the term of this patent is extended or adjusted under 35 U.S.C. 154(b) by 25 days.

(21) Appl. No.: 14/594,985

(22) Filed: Jan. 12, 2015

(65) Prior Publication Data
US 2015/0211651 A1    Jul. 30, 2015

Related U.S. Application Data

(60) Provisional application No. 61/932,591, filed on Jan. 28, 2014.

(51) Int. Cl.
*F16K 17/40* (2006.01)
*B01L 3/00* (2006.01)
*G01N 33/28* (2006.01)

(52) U.S. Cl.
CPC ......... *B01L 3/567* (2013.01); *B01L 2200/0684* (2013.01); *G01N 33/2823* (2013.01); *Y10T 137/1632* (2015.04)

(58) Field of Classification Search
CPC ... E21B 49/001; E21B 49/00; G01N 33/2823; Y10T 137/1632; B01L 3/50
See application file for complete search history.

(56) References Cited

U.S. PATENT DOCUMENTS

| | | | | |
|---|---|---|---|---|
| 2,649,825 A * | 8/1953 | Fisher | ...................... | B25B 13/48 29/213.1 |
| 2,966,190 A * | 12/1960 | Nowotny | ................ | B29C 73/08 152/370 |
| 3,026,904 A * | 3/1962 | Dollison | ............... | F16K 17/044 137/458 |
| 3,289,467 A * | 12/1966 | Parker | .................... | G01N 33/00 210/402 |
| 3,482,594 A * | 12/1969 | Erfried | .................. | F16K 17/046 137/538 |
| 3,718,057 A * | 2/1973 | Berchtold | ............... | B60C 25/18 81/15.4 |
| 4,716,928 A * | 1/1988 | Kussel | .................. | F16K 17/046 137/494 |
| 5,001,434 A * | 3/1991 | Marrelli | ............. | G01N 33/2823 324/640 |
| 5,623,959 A * | 4/1997 | Granmoe | ................ | B25B 13/48 137/322 |
| 6,629,451 B1 * | 10/2003 | Taylor | .................... | G01N 11/14 73/54.28 |
| 6,751,822 B2 * | 6/2004 | Phillipson | ............. | E04H 4/1663 15/1.7 |
| 7,523,648 B2 * | 4/2009 | Zougari | ............. | G01N 33/2823 73/61.62 |
| 2012/0266969 A1 * | 10/2012 | Merchant | ............... | F01N 3/2066 137/14 |
| 2013/0312511 A1 * | 11/2013 | Jamison | ................. | G01N 15/04 73/152.05 |
| 2015/0354300 A1 * | 12/2015 | Jamison | ............. | G01N 33/2823 73/152.25 |

* cited by examiner

*Primary Examiner* — Craig Schneider
*Assistant Examiner* — Kevin Barss
(74) *Attorney, Agent, or Firm* — Keeling Patents & Trademarks, LLC; Kenneth A. Keeling; Melissa M. Martinez

(57) ABSTRACT

A pressure relief tool including a stem connected to a plunger assembly, a plunger rod slidably retained in the plunger assembly and the stem, a stem connector for connecting the stem to a test cell vent opening, a handle operably connected to the plunger rod, and a vent tube extending from said plunger assembly, the vent tube fluidly connected to an annular opening within the stem. A method of opening a blockage and venting pressure from a high temperature high pressure test cell includes attaching a pressure relief tool of the present invention to the test cell vent opening; advancing the plunger rod through the vent opening, puncturing the blockage in the test cell to allow fluid flow to the vent opening, and allowing fluid to exit the test cell through the annular opening in the stem and the vent tube.

18 Claims, 3 Drawing Sheets

Method 200

| Attachment Step 202 |
| Injection Step 204 |
| Puncture Step 206 |
| Release Step 208 |

Figure 5

HTHP PRESSURE RELIEF TOOL

CROSS-REFERENCE TO RELATED APPLICATIONS

This application claims the benefit of U.S. Provisional Application No. 61/932,591 filed on Jan. 28, 2014, which application is incorporated herein by reference as if reproduced in full below.

STATEMENT REGARDING FEDERALLY SPONSORED RESEARCH OR DEVELOPMENT

Not applicable.

FIELD OF THE DISCLOSURE

This invention relates generally to testing equipment used to measure properties of materials and chemical systems, and more specifically to an apparatus and method to clear blockage in a high pressure test cell and safely vent cell contents.

BACKGROUND

In the oil and gas industry, it is necessary to understand the properties of materials used during drilling and exploration and to determine how properties are affected by temperature, pressure and time.

Test cells are variously used to determine properties of chemical systems in relation to time, temperature, and pressure variations relevant to drilling and cementing operations.

During common laboratory testing procedures, mixtures are prepared, inserted in a test cell, and subjected to temperature and pressure variations. A commonly used laboratory device is a high temperature high pressure filter press, sometimes referred to herein as an HTHP filter press. Conventional test cells are generally constructed of stainless steel with upper caps and lower caps. HTHP filter presses are used to determine the characteristics of filtrates expelled under simulated down hole conditions of various fluids used in the industry, such as drilling muds, cement slurries, and completion fluids. Tests are run at temperatures as high as 500° F. and pressures up to 5000 PSI. Due to test design requirements and properties of the fluids being tested, plugging of pressurization ports can occur from time to time. Upon a plugging occurrence, high pressure gases and liquids (i.e., fluids) can be trapped inside the cell.

Currently-practiced methods to clear the plugged vent and release the pressure include using a paper clip or like object to punch through a vent and clear the obstruction, and operating a drill bit extending through a vent. Problematically, these and similar methods require manually clearing the vent and hoping the resulting pressure release, if any, will be not be explosive. Alternatively, elaborate safety stands may be constructed that allow the cell cap to be removed safely, while preventing damage or injury from explosive release of pressure. Currently practiced methods all potentially allow undercontrolled release of gases, liquids, and debris.

BRIEF SUMMARY OF THE DISCLOSURE

Embodiments of the present invention comprise a pressure relief tool and method that allows both safe clearance of obstructions clogging a release vent of a test cell and controlled release of pressure.

Embodiments of the pressure relief tool of the present invention comprise a stem connected to a plunger assembly, a plunger rod slidably retained in the plunger assembly and the stem, a stem connector for connecting the stem to a test cell vent opening, a handle operably connected to an upper rod end, and a vent tube extending from said plunger assembly, with said vent tube fluidly connected to an annular opening intermediate said plunger rod and an inner opening of said stem.

Embodiments of a method of opening a blockage and venting pressure from a high temperature high pressure test cell comprise attaching a pressure relief tool comprising a stem connected to a plunger assembly, a plunger rod slidably retained in the plunger assembly and stem, a stem connector, a plunger handle, and a vent tube to a vent of the test cell; advancing the plunger rod through the vent opening, puncturing the blockage in the test cell to allow fluid flow to the test cell vent opening, and allowing fluid to exit the test cell through a stem opening.

BRIEF DESCRIPTION OF THE DRAWINGS

For a more complete understanding of the exemplary embodiments, reference is now made to the following Detailed Description of Exemplary Embodiments of the Invention, taken in conjunction with the accompanying drawings, in which:

FIG. 5 depicts a method of the present invention.

DETAILED DESCRIPTION OF EXEMPLARY EMBODIMENTS OF THE INVENTION

Figure 1:
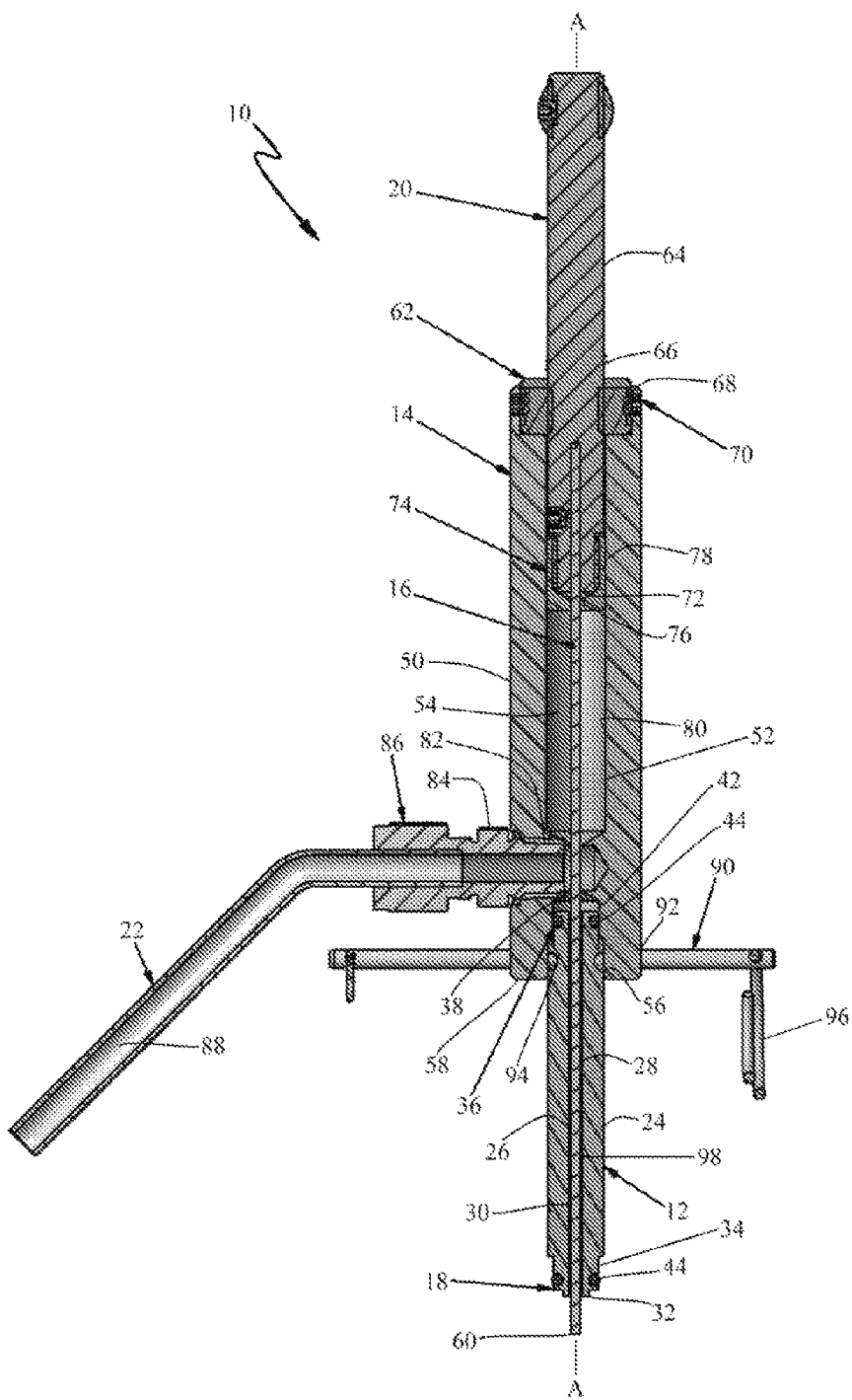
FIG. 1 depicts a cross-sectional view of an embodiment of a pressure relief tool of the present invention.

An exemplary embodiment is best understood by referring to the drawings, like numerals being used for like and corresponding parts of the various drawings.

The directions lower and upper as used in this specification are used for descriptive purposes only and it will be understood by one having skill in the art that different orientations are possible.

As used herein inner or inward means toward the axial center A-A of the pressure relief tool and outer or outward means away from axial center A-A, unless the context indicates a contrary meaning.

Referring to FIG. 1, a cross-sectional view of a pressure relief tool 10 is depicted. Pressure relief tool 10 generally comprises a stem 12 connected to a plunger assembly 14, a plunger rod 16 slidably retained in the plunger assembly 14 and stem 12, a stem connector 18, a handle 20, and a vent tube 22 connected to and extending from said plunger assembly 14.

In an exemplary embodiment of the present invention, plunger assembly 14 comprises an elongated hollow cylindrical body 50 having a cylindrical interior surface 52 defining interior opening 54. Interior opening 54 extends through body 50 along axis A-A. A lower opening 56 is provided proximate lower end 58 of body 50 for connection of assembly 14 to stem 12.

In an exemplary embodiment of the present invention, stem 12 comprises an elongated, substantially hollow cylindrical body 24 having a cylindrical interior surface 26 defining interior channel 28. Interior channel 28 extends throughout body 24 along axis A-A. A lower stem connector 18 is provided proximate a lower end 32 of body 24 for connection of stem 12 to an opening in a test cell (not shown in FIG. 1), such as test cell 100 depicted in FIGS. 2, 3, and 4. In an exemplary embodiment, connector 18 comprises stem threading 34 for engaging corresponding cap threading 104 provided in a vent opening 102 of test cell 100. An upper end 36 of stem 12 is slidably received in a lower opening 56 of plunger assembly 14. An exterior surface 42 of stem 12 upper end 36, and lower opening 56 of plunger assembly 14, are constructed for fit of exterior surface 42 within opening 56. Ring seals 44 are provided proximate upper end 36 of stem 12 for sealing engagement of stem 12 with plunger lower opening 56. Ring seals 44 are provided proximate lower end 32 of body 24 for sealing engagement of lower end 32 with cell vent opening 102.

A safety pin opening 92 is provided in plunger body 50 proximate lower end 58. A safety pin recess 94 is provided in exterior surface 42 of stem 12 proximate upper end 36 of stem 12. A safety pin 90 extends through pin opening 92 of plunger body 50 and through safety pin recess 94 of stem 12. Safety pin 90 retains stem 12 in a fixed vertical orientation in relation to plunger assembly 14 with upper end 36 of stem 12 received in lower opening 56 of plunger assembly 14. Safety pin 90 may be readily removed from pin opening 92 and stem recess 94 by pulling safety pin ring 96, thereby allowing disconnection of plunger assembly 14 from stem 12.

Plunger handle 20 extends into interior opening 54 at an upper end 62 of plunger assembly 14. Plunger handle 20 comprises an elongated rod body 64. External threading 66 is provided on body 64. Internal threading 68 is provided at the upper end 62 of plunger assembly 14. Rod body 64, external threading 66, and internal threading 68 are sized and constructed to allow extension of rod body 64 into and out of interior opening 54 of plunger assembly 14 by rotation of handle 20 in relation to plunger assembly 14. Accordingly, rod body 64 may be extended upwardly or downwardly by screwing rod body 64 in or out of upper end 62.

In an exemplary embodiment, internal threading 68 of interior opening 54 may be accomplished by providing a cylindrical collar 70 retained in plunger body 50, such collar 70 having internal threading 68.

Plunger rod 16 extends from lower end 72 of rod body 64. Plunger assembly 14 and stem 12 are constructed and sized such that interior opening 54 of plunger assembly 14 and channel 28 of stem 12 are aligned. Plunger rod 16 extends through interior opening 54 and channel 28. Plunger rod 16 is aligned along axis A-A. As plunger rod 16 is fixedly attached to handle body 64, movement of handle body 64 upward or downward results in corresponding movement of plunger rod 16 through interior opening 54 and through channel 28.

In an exemplary embodiment, a plunger guide 74 is disposed within body 64. Plunger guide 74 is a substantially hollow cylindrical structured having an opening 76 at its lower end. Opening 76 is sized to allow rod 16 to extend therethrough. Plunger guide 74 is provided with an exterior surface 78 sized and structured to closely fit within interior surface 80 of interior opening 54, thereby centering rod 16 and providing effective sealing between surface 78 and surface 80.

In an exemplary embodiment, rod 16 comprises hardened steel.

A vent opening 82 is provided in plunger body 50. A connector 84 is provided in opening 82. A vent connector 86 is provided on vent tube 22 to allow connection of vent tube 22 to connector 84. Vent tube 22 comprises a substantially hollow tube defining vent channel 88. Opening 82, connector 84, vent connector 86, and vent tube 22 are arranged and sized such that vent tube 22 interior channel 88 is fluidly connected to interior opening 54 of plunger body 50.

Rod 16 is sized and structured in relation to interior channel 28 such that an annulus 30 extends between exterior surface 98 of rod 16 and interior surface 26 of stem 12. Accordingly fluid communication exists through annulus 30 to interior opening 54 and vent channel 88.

Operation

Figure 2:
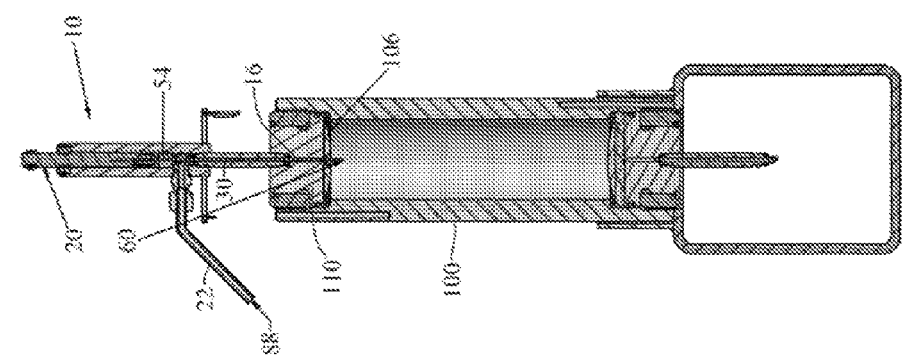
FIG. 2 depicts a cross-sectional view of an embodiment of a pressure relief tool of the present invention proximate a test cell.

Referring to FIG. 2, a plugging event of a test cell 100 is depicted with blockage 106. Pressure relief tool 10 is placed proximate vent opening 102 of test cell 100. Stem 12 connector 18 is positioned to attach to vent opening 102 utilizing cap threading 104.

Figure 3:
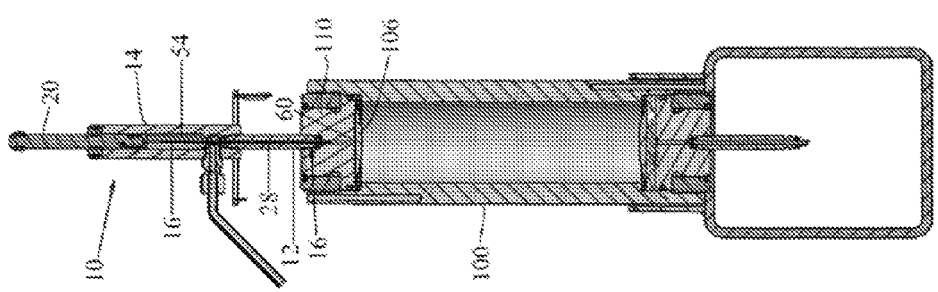
FIG. 3 depicts a cross-sectional view of an embodiment of a pressure relief tool of the present invention engaged with a test cell.
Figure 4:
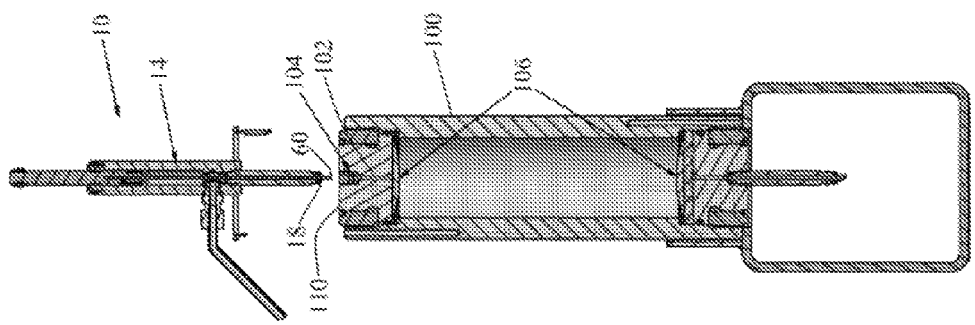
FIG. 4 depicts a cross-sectional view of an embodiment of a pressure relief tool of the present invention engaged with a test cell with the plunger rod extended.

Referring to FIG. 3, pressure relief tool 10 is shown connected to test cell 100 with axis A-A aligned with cell vent opening 102. Handle 20 is then turned in a direction such that handle 20 moves downward, thus advancing plunger rod 16 downward through interior opening 54 and interior channel 28. As depicted in FIG. 3 the lower tip 60 of rod 16 pushes through, thereby puncturing, blockage 106. As depicted in FIG. 4, upon opening of a passage in blockage 106, fluid (not shown in the drawings) under pressure within test cell 100 is released through annulus 30 into interior opening 54 and through vent channel 88.

Accordingly, pressurized fluid within a test cell 100 may be channeled through vent tube 22 to a determined location until pressure within test cell 100 is reduced to a level consistent with safe removal of a cell cap 110.

Method

Referring to FIG. 5, an embodiment of a method 200 of opening a blockage and venting pressure from a high temperature high pressure test cell comprises.

An attachment step 202 of attaching a pressure relief tool, such as pressure relief tool 10 comprising a stem 12 connected to a plunger assembly 14, a plunger rod 16 slidably retained in the plunger assembly 14 and stem 12, a stem connector 18, a handle 20, and a vent tube 22, to a vent opening of the test cell.

An injection step 204 of advancing a plunger rod, such as rod 16, through the vent opening of the test cell.

A puncture step 206 of advancing the plunger rod through the blockage in the test cell to allow fluid flow to the test cell vent opening.

A release step 208 of allowing fluid contained in the test cell to exit the test cell through an opening in the stem, such as annulus 30, and through a venting structure, such as channel 88.

Various embodiments will be understood from the foregoing description, and it will be apparent that, although embodiments have been described in detail, various changes, substitutions, and alterations may be made in the manner, procedure and/or details thereof without departing from the spirit and scope or sacrificing any of its material advantages, the forms hereinbefore described being merely exemplary embodiments thereof.

We claim:

1. A pressure relief tool apparatus for a test cell, comprising:
   a plunger assembly;
   a plunger rod;
   a handle;
   a stem;
   a stem connector; and
   a vent opening; wherein
      said stem is connected to said plunger assembly;
      said plunger rod is slidably retained within said plunger assembly and said stem;
      said stem connector is adapted to connect said stem to a test cell;
      said handle is operably connected to said plunger assembly;
      said plunger rod is adapted to be slidably movable by manipulation of said handle; and
      said vent opening is adapted to provide fluid flow from an annular opening intermediate an exterior surface of said plunger rod and an interior surface of said stem.

2. The pressure relief tool apparatus of claim 1, wherein said stem connector comprises threading adapted to connectively engage corresponding threading in said test cell.

3. The pressure relief tool apparatus of claim 1, further comprising a removable pin; wherein said stem and said plunger assembly are disconnectable from each other by removal of said pin.

4. The pressure relief tool apparatus of claim 1, wherein said handle is threadingly connected to said plunger assembly.

5. The pressure relief tool apparatus of claim 4, wherein said plunger assembly comprises a collar to which said handle is threadingly connected.

6. The pressure relief tool apparatus of claim 1, wherein said vent opening is adapted to provide fluid flow from an annular opening intermediate an exterior surface of said plunger rod and an interior surface of said plunger assembly.

7. The pressure relief tool apparatus of claim 1, further comprising a plunger guide adapted to center said plunger rod in said plunger assembly.

8. The pressure relief tool apparatus of claim 1, further comprising a connector proximate said vent opening for fluidly connecting said vent opening to an external venting structure.

9. The pressure relief tool apparatus of claim 8, wherein said external venting structure comprises one or more components selected from the group consisting of:
   A. a connector;
   B. a vent connector; and
   C. a vent tube.

10. The pressure relief tool apparatus of claim 1, wherein said plunger rod comprises hardened steel.

11. The pressure relief tool apparatus of claim 1, wherein said plunger rod is fixedly attached to said handle.

12. The pressure relief tool apparatus of claim 1, wherein said manipulation of said handle comprises rotation of said handle in relation to said plunger assembly.

13. A method of venting pressure from a test cell, comprising:
   fluidly connecting a pressure relief tool to a test cell;
   wherein said pressure relief tool comprises:
      a plunger rod; and
      a vent opening; and
   wherein said test cell:
      comprises a cell vent opening; and
      contains material disposed therein that prevents fluid flow through said
      cell vent opening; and
   operating said pressure relief tool to advance said plunger rod through said cell vent opening into said test cell to displace at least a portion of said material, thereby permitting fluid flow through said cell vent opening and through said vent opening.

14. The method of venting pressure from a test cell of claim 13, further comprising withdrawing said plunger rod at least partially from said test cell.

15. The method of venting pressure from a test cell of claim 13, wherein said pressure relief tool further comprises a connector proximate said vent opening for fluidly connecting said vent opening to an external venting structure.

16. A method of venting pressure from a test cell, comprising:
   fluidly connecting a pressure relief tool to a test cell;
   wherein said pressure relief tool comprises:
      a plunger assembly;
      a plunger rod;
      a handle;
      a stem;
      a stem connector; and
      a vent opening; wherein
         said stem is connected to said plunger assembly;
         said plunger rod is slidably retained within said plunger assembly and said stem;
         said stem connector is adapted to connect said stem to said test cell;
         said handle is operably connected to said plunger assembly;
         said plunger rod is adapted to be slidably movable by manipulation of said handle; and
         said vent opening is adapted to provide fluid flow from an annular opening intermediate an exterior surface of said plunger rod and an interior surface of said stem; and
   wherein said test cell:
      comprises a cell vent opening; and
      contains material disposed therein that prevents fluid flow through said cell vent opening; and
   operating said pressure relief tool to advance said plunger rod through said cell vent opening into said test cell to displace at least a portion of said material, thereby permitting fluid flow through said cell vent opening and through said vent opening.

17. The method of venting pressure from a test cell of claim 16, further comprising withdrawing said plunger rod at least partially from said test cell.

18. The method of venting pressure from a test cell of claim 16, wherein said pressure relief tool further comprises a connector proximate said vent opening for fluidly connecting said vent opening to an external venting structure.

* * * * *